(12) United States Patent
Verma et al.

(10) Patent No.: US 11,843,756 B2
(45) Date of Patent: Dec. 12, 2023

(54) IMAGE SIGNAL PROCESSING TO COMPENSATE FOR SCENE CHANGES

(71) Applicant: Verily Life Sciences LLC, South San Francisco, CA (US)

(72) Inventors: Nishant Verma, Burlingame, CA (US); Ryan Robertson, Sunnyvale, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 17/447,497

(22) Filed: Sep. 13, 2021

(65) Prior Publication Data

US 2022/0086412 A1 Mar. 17, 2022

Related U.S. Application Data

(60) Provisional application No. 63/077,538, filed on Sep. 11, 2020.

(51) Int. Cl.
*H04N 13/111* (2018.01)
*H04N 13/207* (2018.01)
(Continued)

(52) U.S. Cl.
CPC .......... *H04N 13/111* (2018.05); *A61B 1/0005* (2013.01); *A61B 1/00009* (2013.01);
(Continued)

(58) Field of Classification Search
CPC ..... G09G 2310/027; G09G 2310/0297; G09G 3/3614; G09G 3/3685; G09G 3/3688;
(Continued)

(56) References Cited

U.S. PATENT DOCUMENTS

| 7,453,490 B2 * | 11/2008 | Gunday | H04N 7/18 |
| | | | 348/E7.085 |
| 10,944,947 B2 * | 3/2021 | Kubo | A61B 1/0684 |

(Continued)

OTHER PUBLICATIONS

Debevec et al., "Recovering High Dynamic Range Radiance Maps From Photographs", SIGGRAPH '97 Proceedings of the 24th Annual Conference on Computer Graphics and Interactive Techniques, 1997, 10 pages.

(Continued)

*Primary Examiner* — Behrooz M Senfi
(74) *Attorney, Agent, or Firm* — Kilpatrick Townsend & Stockton LLP (57) ABSTRACT

One example method includes obtaining, from an endoscope and between first and second video frames of a real-time video having a frame rate, a preliminary image of a scene during a surgical procedure, the first image comprising a plurality of pixels, wherein the first and second video frames are consecutive video frames in the real-time video; determining, for each pixel of the plurality of pixels, a depth within the scene; determining first image capture parameters for the scene based on a scene illumination setting and a first set of pixels within a first range of depths in the scene; capturing, between the first and second consecutive output video frames, a first image using the first image capture parameters; determining an illumination correction for a second set of pixels at a second range of depths within the scene; capturing, between the first and second consecutive output video frames, a second image using the illumination correction; generating a composite image based on the first and second images; and outputting the composite image as the second output video frame.

23 Claims, 6 Drawing Sheets

(51) Int. Cl.
*H04N 13/254* (2018.01)
*A61B 1/00* (2006.01)
*H04N 5/265* (2006.01)
*A61B 1/04* (2006.01)
*H04N 23/72* (2023.01)
*H04N 13/00* (2018.01)
*H04N 23/50* (2023.01)

(52) U.S. Cl.
CPC ............ *A61B 1/00193* (2013.01); *A61B 1/04* (2013.01); *H04N 5/265* (2013.01); *H04N 13/207* (2018.05); *H04N 13/254* (2018.05); *H04N 23/72* (2023.01); *H04N 23/555* (2023.01); *H04N 2013/0081* (2013.01)

(58) Field of Classification Search
CPC .. H04N 5/2352; H04N 5/2354; H04N 5/2355; H04N 5/243; H04N 5/265; H04N 5/66; H04N 13/111; H04N 13/207; H04N 13/239; H04N 13/254; H04N 2005/2255; H04N 2013/0081; A61B 1/00009; A61B 1/000095; A61B 1/0005; A61B 1/00193; A61B 1/04; A61B 1/0605; A61B 1/0655

USPC .......................................................... 348/45
See application file for complete search history.

(56) References Cited

U.S. PATENT DOCUMENTS

| | | | |
|---|---|---|---|
| 2009/0259102 A1 | 10/2009 | Koninckx et al. | |
| 2015/0065803 A1* | 3/2015 | Douglas ............. | A61B 1/00045 600/200 |
| 2016/0089013 A1* | 3/2016 | McDowall ........... | A61B 5/0084 600/476 |
| 2017/0039709 A1* | 2/2017 | Yaguchi ............... | G06K 9/6215 |
| 2018/0204528 A1 | 7/2018 | Miyazawa et al. | |
| 2018/0249889 A1 | 9/2018 | Imai | |
| 2020/0229688 A1* | 7/2020 | Yoshino ........... | H04N 5/232133 |
| 2022/0086412 A1* | 3/2022 | Verma .................. | H04N 5/2354 |

OTHER PUBLICATIONS

Application No. PCT/US2021/050026, International Search Report and Written Opinion, dated Dec. 8, 2021, 13 pages.

* cited by examiner

IMAGE SIGNAL PROCESSING TO COMPENSATE FOR SCENE CHANGES

FIELD

The present application generally relates to image processing and more particularly relates to image processing to compensate for scene lighting during surgical procedures.

BACKGROUND

Minimally invasive surgery employs one or more cameras to provide video images to a surgeon who may not otherwise be able to see the surgical site. For example, a surgeon may insert an endoscope through an incision via a trocar into a patient's body and, using light from one or more light sources, capture video of the anatomy within the surgical site as well as tools the surgeon intends to manipulate.

SUMMARY

Various examples are described for image processing to compensate for scene lighting during surgical procedures. One example method includes obtaining, from an endoscope and between first and second video frames of a real-time video having a frame rate, a preliminary image of a scene during a surgical procedure, the first image comprising a plurality of pixels, wherein the first and second video frames are consecutive video frames in the real-time video; determining, for each pixel of the plurality of pixels, a depth within the scene; determining first image capture parameters for the scene based on a scene illumination setting and a first set of pixels within a first range of depths in the scene; capturing, between the first and second consecutive output video frames, a first image using the first image capture parameters; determining an illumination correction for a second set of pixels at a second range of depths within the scene; capturing, between the first and second consecutive output video frames, a second image using the illumination correction; generating a composite image based on the first and second images; and outputting the composite image as the second output video frame.

Another example method includes obtaining, from an endoscope and between first and second video frames of a real-time video having a frame rate, a preliminary image of a scene during a surgical procedure, the first image comprising a plurality of pixels, wherein the first and second video frames are consecutive video frames in the real-time video; determining, for each pixel of the plurality of pixels, a depth within the scene; capturing a plurality of scene-specific images, comprising, for each scene-specific image: determining an illumination correction for a respective set of pixels at a respective range of depths within the scene; capturing, using the illumination correction, the respective scene-specific image; generating a composite image based on the plurality of scene-specific images; and outputting the composite image as the second output video frame.

One example system includes a communications interface; a non-transitory computer-readable medium; and one or more processors communicatively coupled to the communications interface and the non-transitory computer-readable medium, the one or more processors configured to execute processor-executable instructions stored in the non-transitory computer-readable medium to: obtain, from an endoscope using the communications interface and between first and second video frames of a real-time video having a frame rate, a preliminary image of a scene during a surgical procedure, the first image comprising a plurality of pixels, wherein the first and second video frames are consecutive video frames in the real-time video; determine, for each pixel of the plurality of pixels, a depth within the scene; determine first image capture parameters for the scene based on a scene illumination setting and a first set of pixels within a first range of depths in the scene; capture, using the endoscope and between the first and second consecutive output video frames, a first image using the first image capture parameters; determine an illumination correction for a second set of pixels at a second range of depths within the scene; capture, using the endoscope and between the first and second consecutive output video frames, a second image using the illumination correction; generate a composite image based on the first and second images; and output the composite image as the second output video frame.

One example non-transitory computer-readable medium comprising processor-executable instructions configured to cause one or more processors to obtain, from an endoscope and between first and second video frames of a real-time video having a frame rate, a preliminary image of a scene during a surgical procedure, the first image comprising a plurality of pixels, wherein the first and second video frames are consecutive video frames in the real-time video; determine, for each pixel of the plurality of pixels, a depth within the scene; determine first image capture parameters for the scene based on a scene illumination setting and a first set of pixels within a first range of depths in the scene; capture, using the endoscope and between the first and second consecutive output video frames, a first image using the first image capture parameters; determine an illumination correction for a second set of pixels at a second range of depths within the scene; capture, using the endoscope and between the first and second consecutive output video frames, a second image using the illumination correction; generate a composite image based on the first and second images; and output the composite image as the second output video frame.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of image processing to compensate for scene lighting during surgical procedures. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Surgical procedures are frequently performed using minimally invasive techniques, where the surgeon does not fully open the surgical site. Instead, the surgeon may make one or several incisions and insert one or more tools into the surgical site along with a camera, such as an endoscope, to enable the surgeon to perform the surgery. The endoscope may also include its own light source to illuminate the surgical space (or a separate light source may be inserted through an incision) and enable the endoscope to capture and provide video to the surgeon via a display device. Thus, the surgeon is able to view the incoming endoscope video to allow them perform the surgery.

However, surgical sites can be difficult to properly illuminate and thus it can be difficult to capture clear video of all parts of the surgical site. Indeed, one of the key issues in endoscope visualization is non-uniformity in scene brightness, where some parts of the scene are well illuminated but other parts are not. Since illumination originates from the light source and falls off based on the square of the distance, such brightness non-uniformity is expected where anatomy at a greater depth (e.g., the background) reflects much less than anatomy at a lesser depth (e.g., foreground). Moreover, if the anatomy closer to the camera (foreground) occupies the majority of the field-of-view, then auto-exposure functionality in the endoscope, which is responsible for maintaining consistent exposures frame-to-frame, gets driven primarily by the foreground intensities. This can further exacerbate darkening of the anatomy in the background. Alternatively, if the exposure is adjusted to brighten the background features, the foreground can quickly become over-exposed, which can cause the image sensor in the endoscope to saturate. While it is possible to compensate for some underexposed regions by increasing the gain setting on the image sensor's output, noise is also amplified and, in dark areas, may be a significant component of any amplified signal.

To address these issues, an example system generates high dynamic range ("HDR") video frames in real-time and at the desired video frame rate. To do so, for each frame, it captures an initial image and performs depth estimation on every pixel in the image. For stereoscopic endoscopes, it may perform stereo matching between the pixels in the stereoscopic images to estimate depths at each pixel. But for endoscopes with a single image sensor, depth estimation may be performed using a trained machine learning ("ML") model or by projecting structured non-visible light, e.g., infrared light, into the scene and estimate depth based on distortions of the structured light pattern.

After determining depths in the scene for each pixel in the initial image, the system then captures a sequence of several images at a higher frame-rate than the output video frame rate. For example, if output frame rate is 30 frames per second ("fps"), the endoscope may capture images at a rate of 120 fps, which provides four images per video frame. The first of these images may be used for depth estimation. The remaining three images may then be used to generate an HDR video frame.

To generate an HDR video frame, a controller for the endoscope captures the initial image as discussed above and performs depth estimation. It then determines depth segments for the successive images to be captured and assigns each pixel in the initial image to one of the depth segments. In this case, the endoscope will capture three additional images, as discussed above, and so it establishes three depth segments. The first image will be captured using image capture parameters established based on pixels assigned to a first depth segment, which in the case corresponds to the pixels nearest the endoscope. Image capture parameters, such as image sensor integration time and sensor gain, are initially determined using auto-exposure functionality based on the pixels in the first depth segment and a first image is captured using those image capture parameters.

For the subsequent images, the image capture parameters are adjusted based on the inverse-square fall-off in pixel brightness based on distance. Thus, for the second image, pixel depths in the second depth segment are used to determine changes to the image capture parameters needed to capture those pixels with a similar brightness as those pixels in the first depth segment. In this example, the average pixel depths of pixels in the first and second depth segments are determined and the brightness fall-off between the first and second average depths is determined. This fall-off is then used to scale image capture parameters to increase the brightness at the second average pixel depth. For example, the system may increase the amount of light output by the light source in the surgical site. The brightness of the light source may be characterized at various settings, which may then be used to estimate the increased brightness needed from the light source.

The controller may also, or instead, increase an integration time for the image sensor in the endoscope, which increases the amount of time the sensor elements, e.g., photodiodes, accumulate charge based on incident light before they are read out as a value. A longer integration time increases the amount of light received at each sensor element, leading to larger pixel values. Another image capture parameter is the overall gain applied to sensor element outputs, either individually or for rows, columns, or the entire image sensor. The gain may scale a pixel's value by a predetermined amount, irrespective of the raw pixel value.

Once the image capture parameters are determined and applied, such as by adjusting the light source or change image sensor settings in the endoscope, a second image is captured. The image capture parameters are then updated again for the pixels in the third depth segment and a third image is captured. With the adjusted image capture parameters in the second and third images, pixels in the second and third pixel depth segments, respectively, will be illuminated properly, even if pixels in other depth segments are not. Thus, by adjusting one or more of these image capture parameters, the second and third images include properly illuminated pixels at the respective depths in the captured scene.

After capturing the three images using the three different sets of image capture parameters, the controller merges the three images to create a composite image. To merge the images, the controller determines, for each pixel, a weighted average pixel value based on the pixel's value in each of the three images. The weighted average pixel values are then used as the pixel values for the composite image. The controller may also apply a depth-based illumination fall-off correction to the composite image, which uniformly imposes the inverse-square fall-off in pixel brightness with depth across the composite image. The composite image is then output as a video frame to the surgeon viewing the video from the endoscope. Each successive video frame is generated the same way, thus, the surgeon receives an HDR video, where each video frame is constructed from multiple images taken in the time between consecutive video frames.

This example system provides HDR video to the surgeon while maintaining a typical video frame rate, e.g., 24, 25, 30, or 60 fps. Depending on the endoscope and controller, even higher frame rates are possible in some examples. The improved video enables the surgeon to see all aspects of the surgical site without contending with video that is overexposed or underexposed. This can improve surgical performance because the surgeon can see the entire surgical site, rather than only those that are properly illuminated. It can also reduce surgery times by avoiding situations where the surgeon must manually adjust video settings to compensate for over- or under-exposed areas within the video, or by adjusting endoscope positioning to better see those portions of a surgical site.

This illustrative example is given to introduce the reader to the general subject matter discussed herein and the disclosure is not limited to this example. The following sections describe various additional non-limiting examples and examples of image processing to compensate for scene lighting during surgical procedures.

Figure 1:
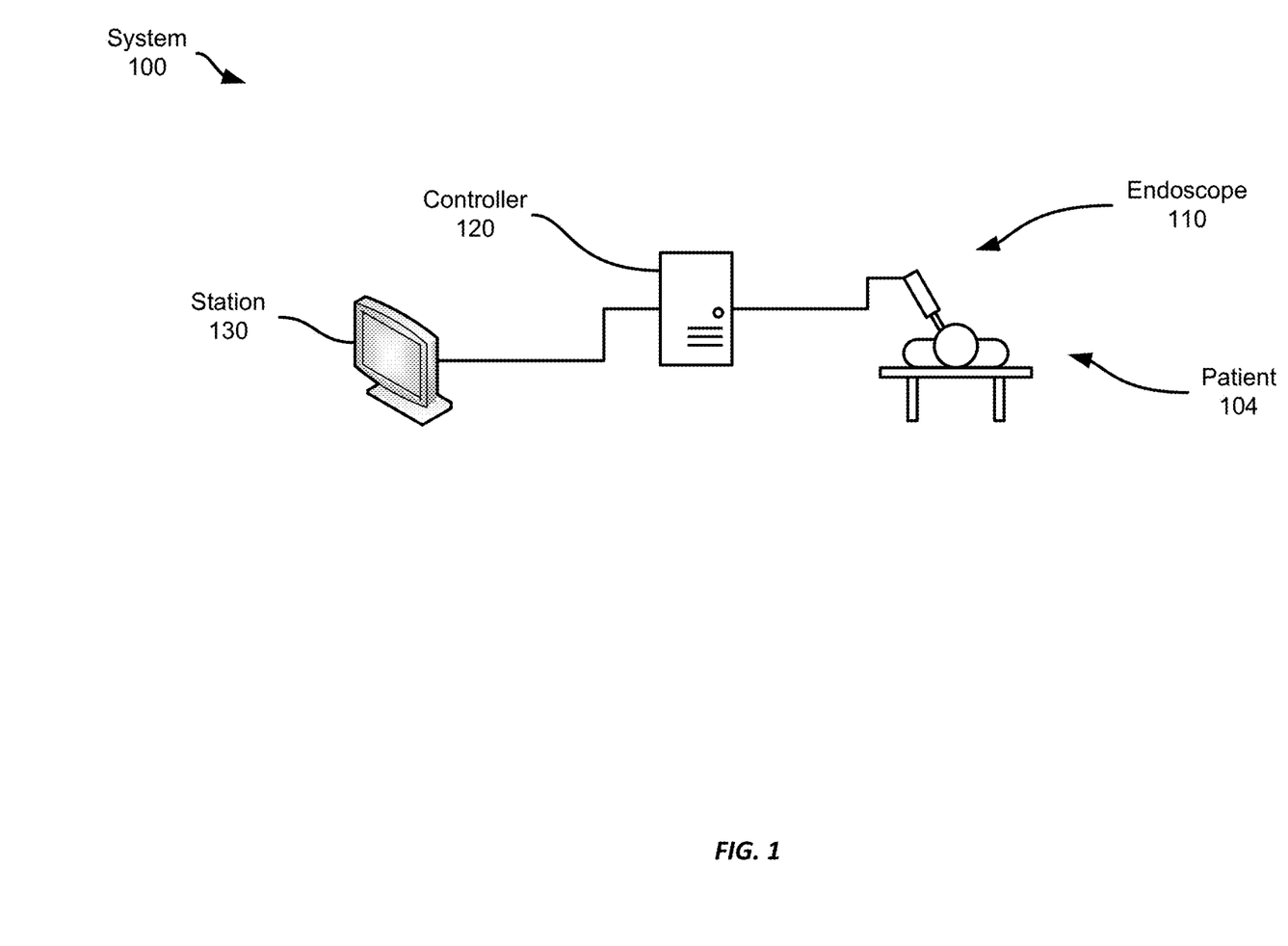
FIGS. 1-4 show example systems for image processing to compensate for scene lighting during surgical procedures.

Referring now to FIG. 1, FIG. 1 shows an example system for image processing to compensate for scene lighting during surgical procedures. The system includes an endoscope 110 and a user station 130, both of which are connected to a controller 120.

The endoscope 110 is any suitable endoscope and may include one or more image sensors, one or more illumination devices, etc. Some examples may employ an endoscope with a single image sensor to capture video images and provide a video stream to the controller 120, which processes them according to various techniques for image processing to compensate for scene lighting during surgical procedures. However, stereoscopic endoscopes are becoming more prevalent and may provide stereoscopic (and simulated 3D) views of the surgical site. The controller 120 then displays resulting video at the user station 130. Using such a system 100, a surgeon may use the endoscope 110 to view a surgical site within a patient 104, such as during a minimally invasive surgery.

Figure 2:
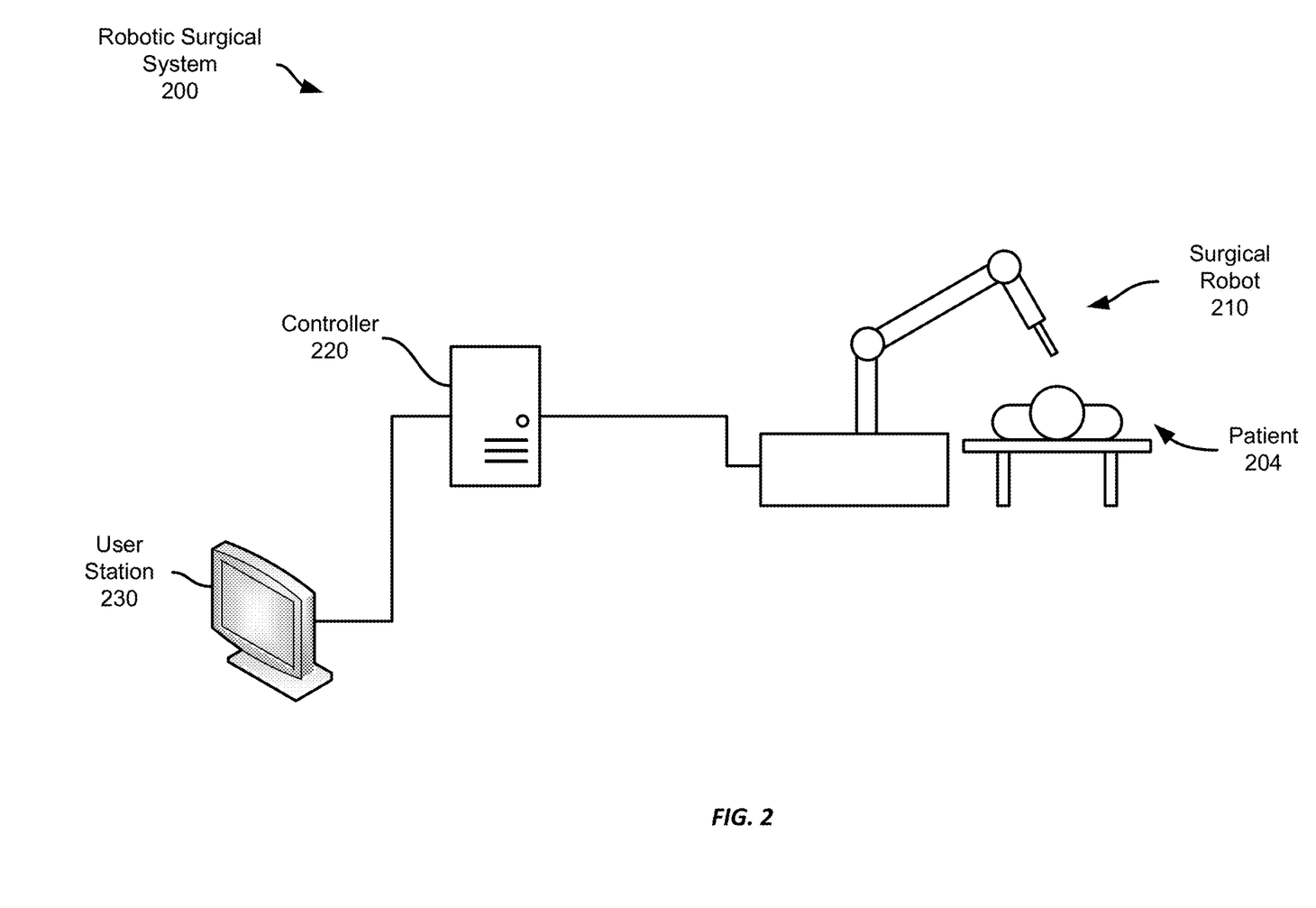

While this example system 100 employs an endoscope 110 to assist a surgeon during a conventional minimally invasive surgical procedure, in some examples the endoscope may be connected to a surgical robotic system that can be used to provide robot-assisted surgery, such as shown in FIG. 2.

In FIG. 2, the example system 200 system includes surgical robotic system. The surgical robot 210 is any suitable robotic system that can be used to perform surgical procedures on a patient, e.g., patient 204, to provide simulations of surgical procedures, or to provide training functionality to allow a surgeon to learn how to control a surgical robot 210, e.g., using exercises to train particular movements or general dexterity, precision, etc. It should be appreciated that discussions throughout this detailed description related to surgical procedures are equally applicable to simulated procedures or training exercises using a surgical robot 210.

A surgical robot 210 may have one or more articulating arms connected to a base. The arms may be manipulated by a controller 220 via inputs received from the user station 230, which may include one or more user interface devices, such as joysticks, knobs, handles, or other rotatable or translatable devices to effect movement of one or more of the articulating arms, as well as one or more display devices to display information to the surgeon during surgery, e.g., video from an endoscope, information from patient medical records, previously obtained images (e.g., X-rays, MRI images, etc.). The articulating arms may be equipped with one or more surgical instruments to perform aspects of a surgical procedure. Different surgical robots 210 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without articulating arms, such as for endoscopy procedures, may be employed according to different examples.

The controller in this example includes a computing device in communication with the surgical robot 210 and is able to control access and use of the robot. For example, the controller 220 may require that a user authenticate herself before allowing access to or control of the surgical robot 210. As mentioned above, the controller 220 may include, or have connected to it, e.g., via user station 230, one or more user input devices capable of providing input to the controller, such as a keyboard, mouse, or touchscreen, capable of controlling the surgical robot 210, such as one or more joysticks, knobs, handles, dials, pedals, etc.

During a surgical procedure, one or more tools may be connected to the surgical robot 210 that may then be inserted into the patient's body to perform different aspects of the surgical procedure. To enable the surgeon to perform the surgery, an endoscope 310 may be connected to the surgical robot 210 and inserted in to the patient 204. Images captured by the endoscope may be communicated to the controller, which processes the images to generate video, as will be described in more detail below, then presents the video to the surgeon at the user station 230. Based on the video, the surgeon can manipulate the surgical robot to cut tissue, ablate, cauterize, etc.

Figure 3:
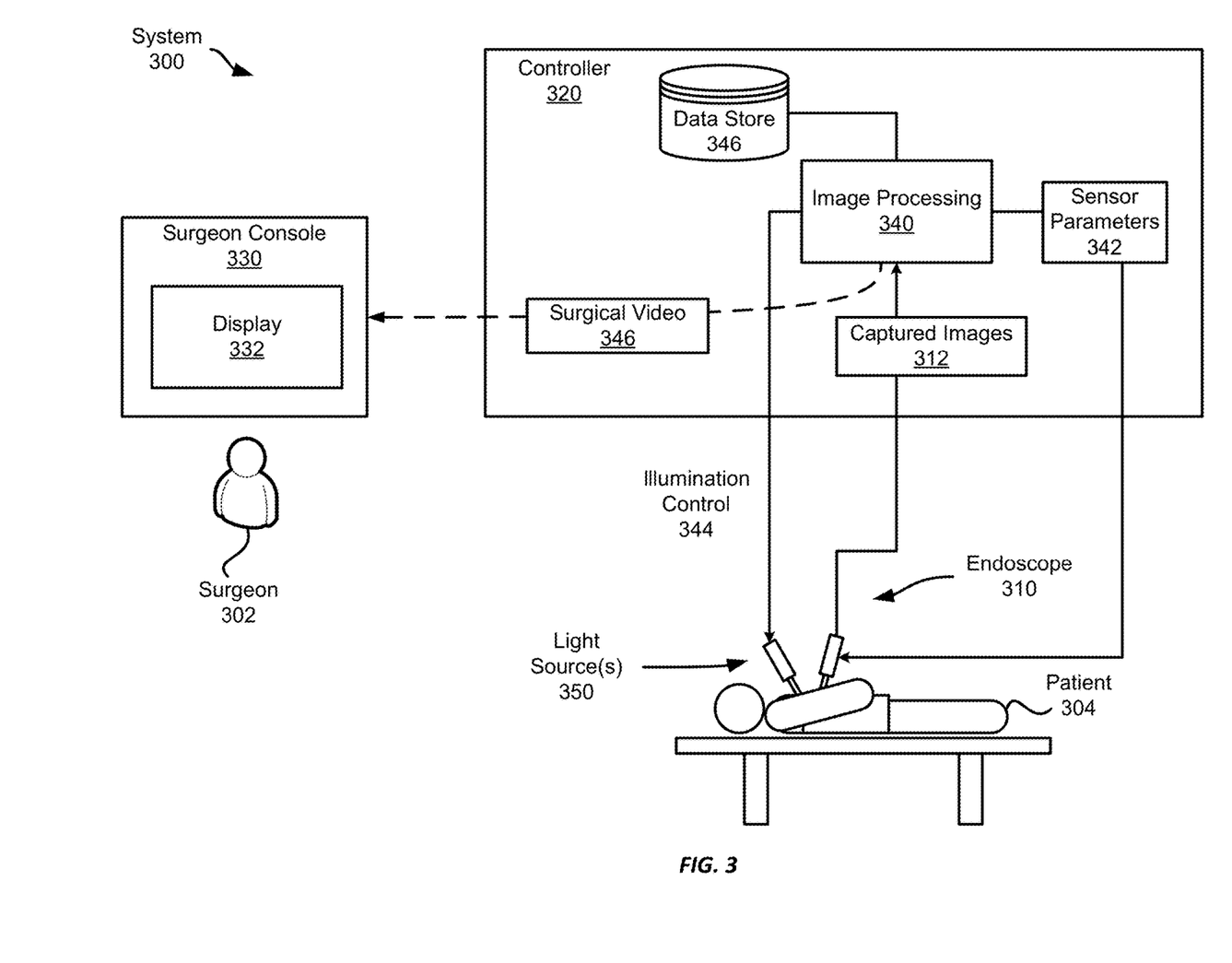

Referring now to FIG. 3, FIG. 3 shows an example system for image processing to compensate for scene lighting during surgical procedures. Similar to the example system 100 shown in FIG. 1, the system 300 in FIG. 3 includes an endoscope 310, a controller 320, and a surgeon console 330, which includes a display 332 and is used by surgeon 302. The endoscope 310 in this example includes a light source, but additional light source(s) 350 may be used as well, at least one of which may be a structured light source.

The controller 320 includes an image processing software component 340, which receives captured images from the endoscope 310 and generates surgical video 346, which is transmitted to the surgeon console 330 and displayed on the display 332, as will be described in more detail below. In addition, the image processing software component 340 also adjusts sensor parameters 342 of the endoscope 310 and provides illumination control signals 344 to the light source(s) 350 to control their respective outputs. In this example, the endoscope 310 includes a light source, so image processing software component 340 may also transmit illumination control signals 344 to the endoscope 310.

And while this example system 300 does not include a surgical robotic system, in some examples, the image processing software component 340 may be executed by a controller (or other computing device) as a part of a surgical robotic system, such as the system 200 shown in FIG. 2.

During operation, the controller 320 employs the image processing software component 340 to configure and operate the endoscope, as well as light sources to illuminate the surgical site, to capture images during a surgery. The image processing software component 340 receives the captured images 312 from the endoscope and generates composite images as will be described in detail below. The composite images are then provided as video frames of surgical video 346 to the surgeon console 330.

When the surgeon begins a surgical procedure, they may make one or more incisions in the patient through which the endoscope 310, light sources 350, and surgical tools may be inserted. During the surgery, the surgeon 302 views video captured by the endoscope 310 on the display 332 to view the surgical site within the patient 304.

To provide high quality surgical video, rather than capturing images and providing them to the display, the image processing software component 340 captures multiple images per video frame and generates a composite image based on those images. The composite image is then output as the video frame, with each successive video frame generated according to the same process. Thus, the image processing software component 340 configures the endoscope to capture images at a rate faster than the frame rate for the surgical video to be provided to the surgeon console 330 and outputs composite images as video frames.

The image processing software component 340 determines a frame rate for the surgical video 346, e.g., from a user setting. It then configures the endoscope 310 to capture images at a higher rate than the determined video frame rate. The higher rate may be determined based on the frame rate for the surgical video and the maximum frame rate supported by the endoscope, or by a number of images to be used to generate a video frame, depending on the capabilities of the endoscope. For example, if the desired frame rate is 30 fps, and the endoscope has a maximum capture rate of 240 fps, the image processing software component 340 may select any higher frame rate between 30 and 240 fps and consequently use any number of images captured between video frames at that higher rate.

For endoscopes with slower maximum frame rates, e.g., 60-90 fps, the number of images to be captured may be limited to two or three. For higher-speed endoscopes, a greater number of images may be captured, e.g., five or more. Further, for such higher-speed endoscopes, only some of the captured images may be used to generate a video frame. For example, an endoscope capturing images at 240 fps may capture eight images per 30 fps video frame, but the image processing software component 340 may only employ the first three to generate a video frame, leaving ⅝ of the video frame time for time to perform portions of the image processing, such as merging the captured frames to generate the next video frame. Such embodiments may provide reduced latency between capturing a first image and outputting a video frame to the surgeon console 330.

To provide the composite video frames, the endoscope 310 needs to capture at least two frames in the time period between consecutive surgical video frames: one frame may be used both for depth estimation and as a first frame for compositing, and a second frame to be used for compositing with the first frame, as will be discussed in detail below. In some examples, however, more than two frames may be used. Hardware limitations may dictate the number of frames that may be captured per video frame, as discussed above. But with a sufficiently high-performance endoscope and controller, as many as five or more images may be captured, processed, and composited to provide a video frame.

To generate a frame of video, the image processing software component 340 selects a video frame rate and an image capture frame rate. It then configure the endoscope 310 to capture images at the image capture frame rate. For purposes of this example, the image capture frame rate is set at four times the video frame rate; however, any suitable image capture frame rate may be employed. The images captured by the endoscope are provided to the image processing software component 340 and stored in a data store 346, such as system memory for the controller 320. It should be appreciated that the image processing software component may begin processing incoming captured images 312 immediately after receiving them, or it may store them and process them once all captured images for a video frame have been received. Further it should be appreciated that some endoscopes may be stereoscopic and so each image sensor in the endoscope may generate an image at the configured frame rate. However, the image processing software component 340 may process each sensor's images independently of each other to provide a stereoscopic surgical video. Thus, the techniques described herein are equally applicable to endoscopes with only a single image sensor or those with multiple image sensors.

In this example, the image processing software component 340 performs depth estimation on a captured image. In this example, the first captured image for a new video frame is used for depth estimation, however, any captured image may be employed. Depth estimation is performed using a trained machine learning model on the identified image in this example and generates a depth value for each pixel in the captured image; however, other techniques may be employed. For example, one of the light sources 350 may be configured as a structured light source that projects a structured light pattern onto the scene. The structured light pattern is reflected by the objects in the scene and is received by the image sensor. Distortions in the structured light pattern will be based on varying depths of objects in the scene and thus, the distortion may be used to determine depths corresponding to each pixel in the scene.

In embodiments that employ a stereoscopic endoscope, pixels in captured stereoscopic images may be analyzed to identify a correspondence between them, e.g., they both represent the same point in the scene, using a process called stereo matching or co-registration. By co-registering pixels between the stereoscopic images, the corresponding depth in the scene may be determined. Once pixels are co-registered between the images, their respective offset from each other in the two images is measured and, using a known distance between the two image sensors and a focal length of the cameras, the distance to the corresponding point in the scene may be determined using the equation: $d(x) = f \times B / (x_{Left} - x_{Right})$ This may be performed for every pixel in each image to generate, for each pixel, a corresponding depth in the scene and the collection of the pixel depths in a scene, however determined, may be referred to as a "depth map."

After the pixel depths have been determined, the image processing software component 340 determines subsets of pixels based on their respective depths. The subsets may be determined based on evenly spaced depth thresholds or may be unevenly spaced and based on clusters of pixels at different depths.

To determine subsets having evenly spaced depth thresholds in one example, the image processing software component 340 determines the minimum and maximum depths represented in the scene and establishes depth thresholds at depths divide the range into a corresponding number of equal sub-ranges. For example, if three images are to be captured for compositing, three subsets are established, each representing the same amount of change in depth in the scene, e.g., in a scene with a maximum depth of 15 cm, the first subset represents depths from 0 to 5 cm, the second represents depths from 5 to 10 cm, and the third represents depths from 10-15 cm, irrespective of the number of pixels falling into any of the subsets. In another example, the system generates subsets with equal numbers of pixels per subset, which may result in subsets having different ranges of depths in the scene.

In a further example, the system may generate subsets based on image capture parameter changes needed to properly illuminate pixels at varying depths. For example and as will be discussed in more detail below, changes may be made to scene illumination, sensor integration time, sensor gain, etc. to capture different depths in the scene. Subsets may be generated based on depth thresholds based on changes to image capture parameters needed at different depths. For example, if a illumination from a light source may be increased without changing either sensor integration time or sensor gain, a first subset may be established based on an initial illumination level established for the foreground, e.g., based on auto-exposure control. A second subset may be established based on scene illumination with the light source outputting its maximum brightness, but without affecting sensor integration time or sensor gain. And a third subset may be generated for the remaining pixels in the scene. Depending on the number of subsets needed, a further subset may be generated for pixels requiring increased sensor integration time, but not requiring increased sensor gain, and finally for a subset requiring both increased sensor integration time and increased sensor gain.

Once the pixel subsets have been established, image capture parameters for each subset may be determined, if they have not already been, such as discussed above. For the initial image in this example, image capture parameters are established based on auto-exposure metering on the pixels in the subset of pixels nearest the camera. As mentioned above, image capture parameters may include the brightness of one or more light sources (such as may be incorporated into the endoscope or separately introduced into the surgical site), image sensor integration time, image sensor gain, etc. These settings may then be established automatically by the camera's auto-exposure functionality to establish a baseline exposure, referred to as $E_{base}$. Subsequent exposures corresponding to subsets of pixels with greater depths may then be determined based on $E_{base}$.

As discussed above, illuminance in a scene falls off as a function of the square of the distance into the scene. Thus, to properly illuminate regions corresponding to pixels in subsequent subsets, the base exposure may be modified according to the respective change in distance between the nearest subset of pixels and the other subsets. If the distances for the subsets, in increase order of depth, are denoted by $d_n$, the exposure settings for the second nearest subset may be established based on $E_{base}*(d_2/d_1)^2$, while any arbitrary subset may be established by $E_{base}*(d_n/d_1)^2$. Based on these relationships, scene lighting, sensor integration time, sensor gain, or a combination of these may be adjusted to obtain an equivalent amount of pixel brightness at each subset of pixels as obtained for the nearest subset of pixels. For example, depending on the scene lighting capabilities, the brightness of the scene lighting may be increased four-fold to obtain a corresponding level of pixel brightness for a subset of pixels twice the distance from the camera as the nearest subset. Alternatively, doubling the scene brightness via light sources and doubling the sensor integration time may achieve a similar effect. It should be noted that because sensor gain amplifies noise as well as the desired signal, some embodiments may adjust available light sources and sensor integration time to the exclusion of adjusting sensor gain, until the both the light sources and sensor integration time have reached their maximum limits.

Once image capture parameters have been determined for each subsequent image to be captured, the different sets of image capture parameters are applied to the light source(s) 350 or endoscope 310 and the corresponding images are captured. As discussed above, in some examples, the initial image used to perform pixel depth determination may be re-used as the initial image capture using $E_{base}$ image capture parameters.

Once the subsequent images 312 have been captured and received by the image processing software component 340, it merges the captured images into a single composite image. In some examples, because images are captured at a high rate (e.g., greater than 60 fps), and are used to generate video frames streamed, which are also output at a substantial frame rate, e.g., 30-60 fps or more, motion between captured images may be ignored when generating a composite image from the captured images. However, in some examples, the image processing software component 340 may perform image alignment of the captured images prior to merging them.

Different examples according to this disclosure may employ different techniques to merge the pixels. One example employs intensity-based weighting of the different captured images. The generalized formula for performing such intensity-based weighting, per pixel, is as follows:

$$hdr(x) = \frac{\sum_{i=1}^{N} w_i(x) \times (I_i(x)/E_i)}{\sum_{i=1}^{N} w_i(x)}.$$

Where captured images are identified as $I_n$, and x corresponds to a pixel location in the composite image and the corresponding pixel location in the captured images. The weights, $w_n(x)$, for a pixel may be determined according to the following formula:

$$w_i(x) = \min(I_i(x) - I_{min}, I_{max} - I_i(x)).$$

This will generate a higher dynamic range image but with illumination fall-off present with depth. However, combining the multiple exposure frames together significantly improves signal-to-noise ratio ("SNR") in the dark regions of the image. Therefore, a digital illumination fall-off correction can be applied to create a uniformly illuminated HDR image:

$$hdr(x) \times \left(\frac{d(x)}{d_1}\right)^2,$$

where d(x) denotes the depth estimated at pixel x in the image domain.

Another example technique to merge the captured images into a composite image employs depth-based weighting of the different captured images. To perform depth-based weighting, per-pixel weights are determined based on corresponding determined pixel depths. In this example, two images frames are linearly combined for all pixels in a particular depth range according to the following:

$$hdr(x) = \begin{cases} I_i(x) \times \left(\dfrac{d(x)}{d_i}\right)^2, & \text{if } I_j(x) \geq I_{max} \\ w_i(x) \times I_i(x) + w_j(x) \times I_j(x), & \text{if } I_{min} < I_i(x), I_j(x) < I_{max} \\ I_j(x) \times \left(\dfrac{d(x)}{d_j}\right)^2, & \text{if } I_i(x) \leq I_{min} \end{cases}$$

$I_i$ and $I_j$ represent two captured images corresponding to depths $d_i$ and $d_j$ in the scene, and are combined for all pixels, x, having a depth, d, in the depth range $[d_i, d_j]$. The pixel weights, $w_n(x)$, are defined according to the following:

$$w_i(x) = \frac{d(x)^2 - d_j^2}{d_i^2 - d_j^2}$$

In the techniques described above, $I_{max}$ and $I_{min}$ denote clipping thresholds typically set as $I_{max}=2^B-1$ and $I_{min}=0$ where B is bit-depth of the RAW sensor data. When none of the exposure frames Ii and $I_j$ are clipped, a weighted combination ensures constant brightness of an object across all scene depths. However, if the higher exposure frame $I_j$ gets clipped at $I_{max}$, the HDR output is generated by correcting illumination drop-off in the lower exposure frame L. Conversely if the lower exposure frame $I_i$ gets clipped at $I_{min}$, then the HDR output is generated by correcting for illumination drop-off in the higher exposure frame $I_j$. This approach generalizes for any number of exposure frames $I_1$, $I_2$, . . . , $I_n$ collected for HDR where exposures $I_i$ and $I_j$ are used to generate HDR outputs for all pixels, x, whose depths are in the range $d(x) \in [d_i, d_j]$. As such, HDR output for all pixels at depths $d \in [d_1, d_2]$ is computed using exposures $I_1$ and $I_2$. Similarly, HDR output for all pixels at depths $d \in [d_2, d_3]$ is computed using exposures $I_2$ and $I_3$ and so on for every depth in the scene.

Once the composite image has been generated by the image processing software component 340, it is provided to the surgeon console 330 as a video frame of the surgical video 346, and the image processing software component begins generating the next video frame. It should be appreciated that in cases with a stereoscope endoscope (or other stereoscopic camera), the same process may be performed in parallel on the respective stereoscopic images to generate composite stereoscopic video frames.

The adaptive HDR approaches discussed above are able to generate a uniformly exposed HDR output image with only few captured images needed. This allows practical implementation of adaptive HDR in endoscope visualization, which has high frame rate and low latency video requirements. Besides uniform exposure in the scene, adaptive HDR also strives to achieve the best possible SNR in any given scene. This is because adaptive HDR selects a set of scene depths targeted to be suitably exposed based on the distribution of depths in the current scene.

In addition to these advantages, scenes where anatomy is present mostly at a single depth, adaptive HDR captures N frames at very similar camera exposure values. When combined together, the resulting HDR output has significantly lesser noise than any of the exposure frames improving the SNR. On the other hand, in scenes where anatomy is present at varying depths, adaptive HDR captures N frames using different camera exposures such that all depths are suitably exposed in at least one exposure frame. When combined together, higher weighting of well-exposed pixels over poorly-exposed pixels ensures better SNR in the output HDR image.

Figure 4:
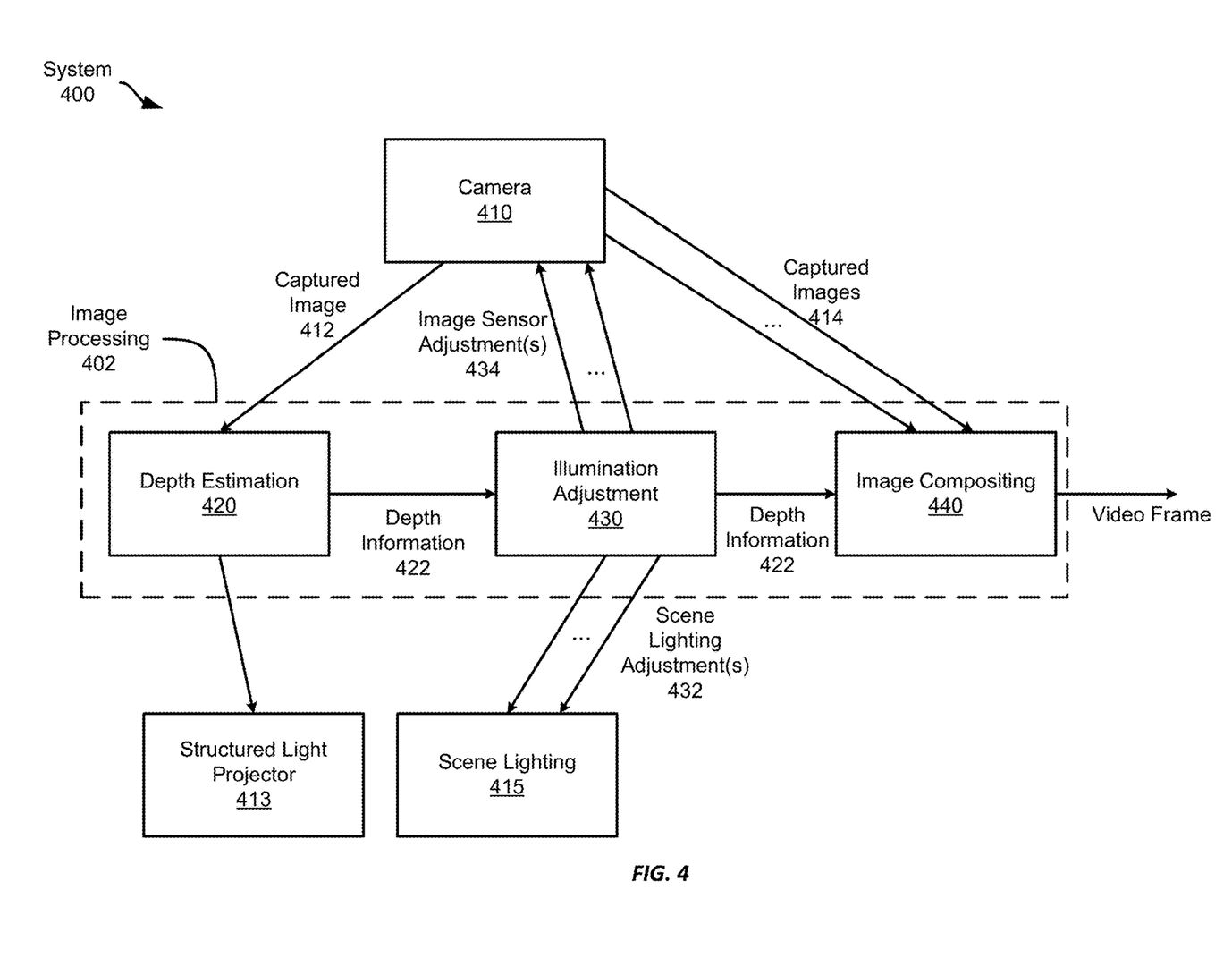

Referring now to FIG. 4, FIG. 4 shows an example system 400 for image processing to compensate for scene lighting during surgical procedures. The system 400 illustrates interactions between portions of the image processing software component 402 and with hardware components, such as the camera 410, a structured light projector 413, and one or more scene lighting sources 415. To generate a video frame, the image processing software component 402 obtains an initial captured image 412 from the camera 410, and employs depth estimation component 420 to determine the depths of each pixel in the captured image 412, generally as described above with respect to FIG. 3. In examples where depth estimation employs structured light, the depth estimation component 420 may also activate the structured light projector 413 to project a structured light pattern into the scene; however some examples may lack a structured light generator, and thus may employ other techniques discussed herein.

The depth estimation component 420 generates and provides depth information 422 to the illumination adjustment component 430, which successively adjusts image capture parameters for subsequent captured images 414 and applies any image sensor adjustments 434, e.g., adjustments to sensor integration time or sensor gain, to the camera 410 and any scene lighting adjustments 432 to the scene lighting source(s) 415.

The image compositing component 440 receives the captured images from the camera, which may include captured image 412 in some examples, and the depth information 422. While in the example, the illumination adjustment component 430 provides the depth information 422 to the image compositing component 440 it may be provided in any suitable way, e.g., directly from the depth estimation component 420. After receiving the captured images 414, the image compositing component generates a video frame (or in examples having stereoscopic cameras, two video frames) based on the captured images 414 and the depth information 422, generally as described above with respect to FIG. 3. The image compositing component 440 then outputs the generated video frame(s).

While this example system 400 shows particular components arranged in a particular way, no specific architecture or design is required. The various components of the image processing software component 402 may be combined or further subdivided into additional components. Further, while explicit transfer of information is depicted, e.g., depth information 422 been sent from the depth estimation component 420 to the illumination adjustment component 430, such transfer may be indirect, such as by storing the depth information in an in-memory data store and subsequently retrieving it as needed.

Figure 5:
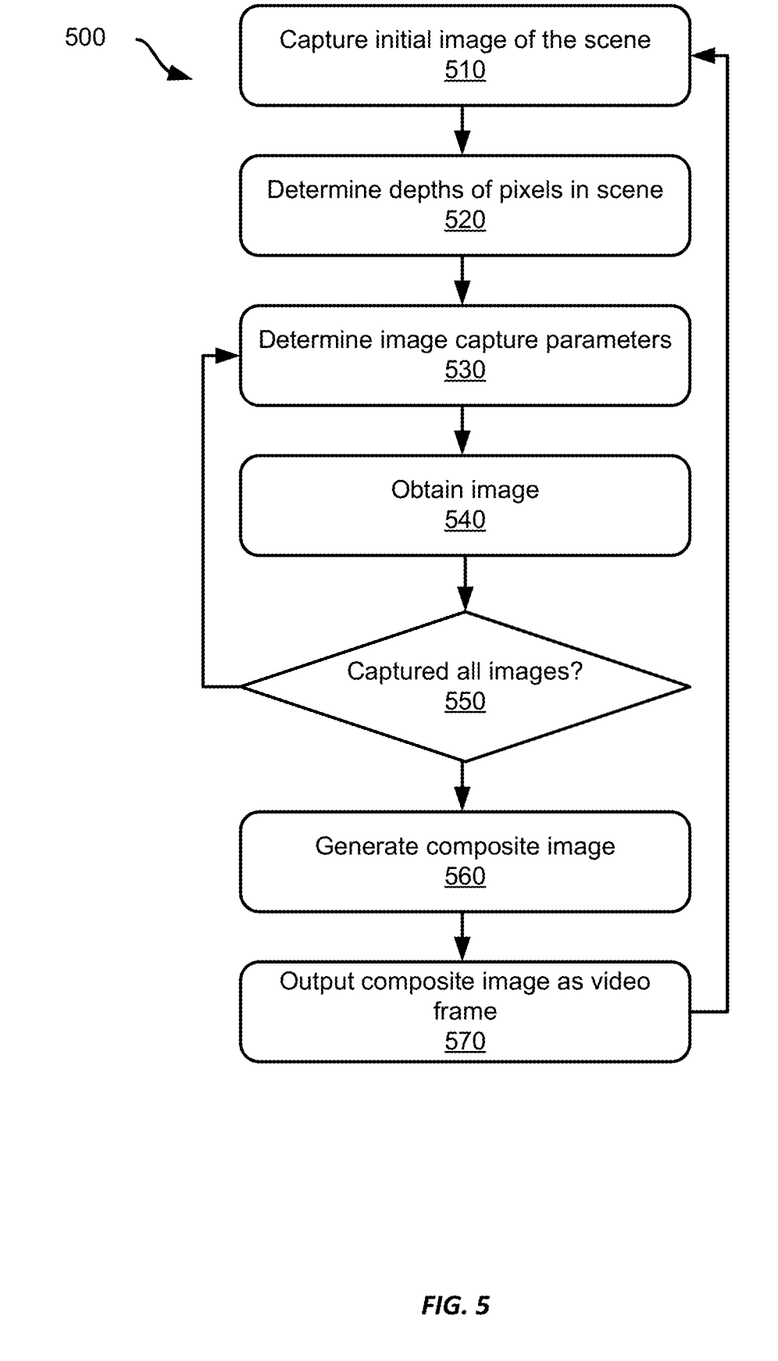
FIG. 5 shows an example method for image processing to compensate for scene lighting during surgical procedures.

Referring now to FIG. 5, FIG. 5 shows an example method for image processing to compensate for scene lighting during surgical procedures. The method will be described with respect to the system 300 shown in FIG. 3; however, any suitable system according to this disclosure may be used to perform methods according to this disclosure.

At block 510, the system 300 uses the endoscope 310 to obtain an initial image, generally as discussed above with respect to FIG. 3. In examples where the endoscope has stereoscopic cameras, the system captures stereoscopic images at substantially the same time.

At block 520, the image processing software component 340 determines depths of pixels in the scene generally as described above with respect to FIG. 3.

At block 530, the image processing software component 340 determines image capture parameters for a subsequent image generally as described above with respect to FIG. 3. The image capture parameters are then provided to the endoscope or to one or more light sources, such as described above with respect to FIG. 3 or 4.

At block 540, the system 300 uses the endoscope 310 to obtain an image (or stereoscopic images) using the image capture parameters generally as described above with respect to FIG. 3.

At block 550, the system 300 determines if all images to generate a video frame have been captured. As discussed above with respect to FIG. 3, the system 300 may determine a number of images to be captured to generate a video frame based on the video frame rate and the camera's maximum frame rate. Alternatively, the number of images may be pre-determined so long as it is within the operational capabilities of the camera. At block 550, if all images have been captured, the method 500 proceeds to block 560. Otherwise, it returns to block 530.

At block 560, the image processing software component 560 generates a composite image generally as discussed above with respect to FIG. 3. In examples that employ stereoscopic cameras, the image processing component 560 generates two composite images, one each for each image sensor of the stereoscopic camera using the images captured by the corresponding image sensor at block 540.

At block 570, the image processing software component 570 outputs the composite image as a video frame generally as described above with respect to FIG. 3. If a stereoscopic camera is used, two video frames will be output, one each per image sensor, to provide HDR stereoscopic video to the surgeon console 330.

After outputting the video frame(s), the method 500 returns to block 510, thus allowing the method 500 to generate, over time, a stream of HDR video frames at the desired video frame rate to provide high quality video to the surgeon performing a surgical procedure. Thus, each execution of blocks 510 to 570 occurs in real time and at a sufficiently high rate to generate and output video frames at block 570 to substantially maintain the desired video frame rate.

Figure 6:
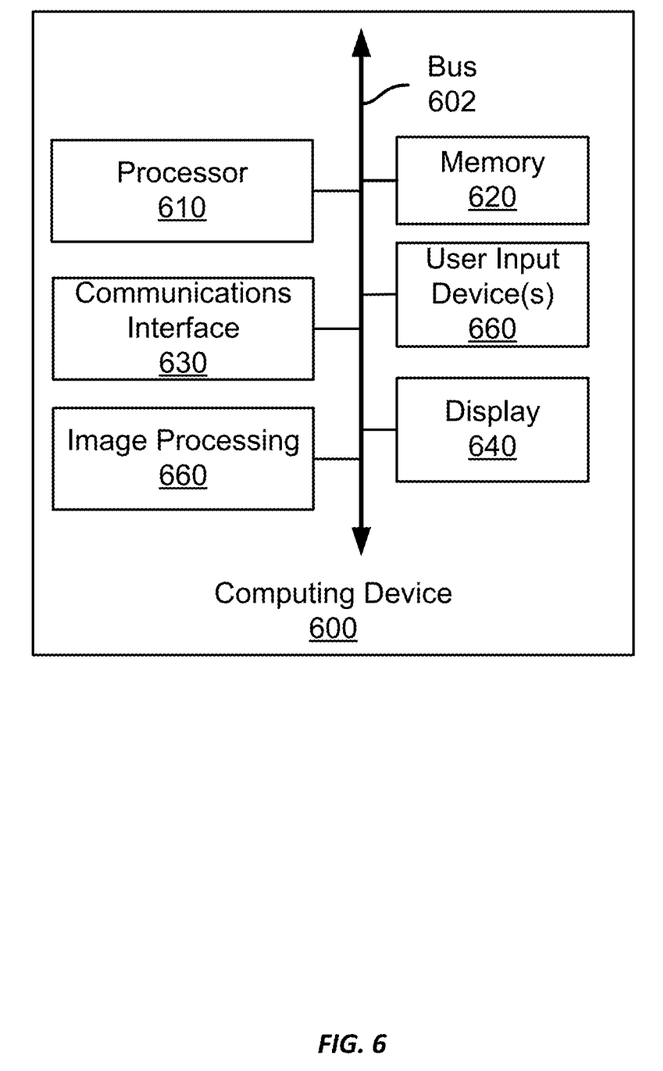
FIG. 6 shows an example computing device suitable for use with systems and methods for image processing to compensate for scene lighting during surgical procedures.

Referring now to FIG. 6, FIG. 6 shows an example computing device 600 suitable for image processing to compensate for scene lighting during surgical procedures. The example computing device 600 includes a processor 610 which is in communication with the memory 620 and other components of the computing device 600 using one or more communications buses 602. The processor 610 is configured to execute processor-executable instructions stored in the memory 620 to perform one or more methods for image processing to compensate for scene lighting during surgical procedures according to different examples, such as part or all of the example method 500 described above with respect to FIG. 5. The computing device, in this example, also includes one or more user input devices 650, such as a keyboard, mouse, touchscreen, microphone, etc., to accept user input. The computing device 600 also includes a display 640 to provide visual output to a user.

In some examples, the computing device 600 also includes an image processing software component 660. Such functionality may be implemented according to various examples according to this disclosure, such as the example image processing software components 340, 402 shown in FIGS. 3 and 4.

The computing device 600 also includes a communications interface 640. In some examples, the communications interface 630 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) or graphical processing unit (GPU) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
  obtaining, from an endoscope and between first and second output video frames of a real-time video having a frame rate, a preliminary image of a scene during a surgical procedure, the preliminary image comprising a plurality of pixels, wherein the first and second output video frames are consecutive video frames in the real-time video;
  determining, for each pixel of the plurality of pixels, a depth within the scene;
  determining first image capture parameters for the scene based on a scene illumination setting and a first set of pixels within a first range of depths in the scene;
  capturing, between the first and second output video frames, a first image using the first image capture parameters;
  determining an illumination correction for a second set of pixels at a second range of depths within the scene;
  capturing, between the first and second output video frames, a second image using the illumination correction;
  generating a composite image based on the first and second images; and
  outputting the composite image as the second output video frame.

2. The method of claim 1, further comprising:
  determining a second illumination correction for a third set of pixels at a third range of depths within the scene;
  capturing, between the first and second output video frames, a third image using the second illumination correction; and
  wherein generating a composite image is further based on the third image.

3. The method of claim 1, wherein:
  obtaining the preliminary image comprises obtaining stereoscopic preliminary images;
  determining the depth within the scene comprises determining, for each pixel of each stereoscopic preliminary image, the depth within the scene,
  capturing the first image comprises capturing stereoscopic first images;
  capturing the second image comprises capturing stereoscopic second images;
  generating the composite image comprise generating composite stereoscopic images from the first and second stereoscopic images; and
  outputting the composite image comprises outputting the composite stereoscopic images.

4. The method of claim 1, wherein the illumination correction comprises one or more of (i) adjusting a light source, (ii) adjusting an image sensor integration time, or (iii) adjusting an image sensor gain.

5. The method of claim 1, further comprising projecting structured light onto the scene, and wherein determining, for each pixel of the plurality of pixels, the depth within the scene is based on detecting the structured light in the preliminary image.

6. The method of claim 1, wherein determining, for each pixel of the plurality of pixels, the depth within the scene, comprising using a machine learning model to estimate, for each pixel of the plurality of pixels, the depth within the scene.

7. The method of claim 1, further comprising determining the first and second ranges of depths based on a total number of pixels in the preliminary image and a number of images to be captured between the first and second output video frames.

8. The method of claim 1, wherein the preliminary image and the first image are the same image.

9. A method comprising:
  obtaining, from an endoscope and between first and second video frames of a real-time video having a frame rate, a preliminary image of a scene during a surgical procedure, the preliminary image comprising a plurality of pixels, wherein the first and second video frames are consecutive video frames in the real-time video;
  determining, for each pixel of the plurality of pixels, a depth within the scene;
  capturing a plurality of scene-specific images, comprising, for each scene-specific image:
    determining an illumination correction for a respective set of pixels at a respective range of depths within the scene;
    capturing, using the illumination correction, the respective scene-specific image;
  generating a composite image based on the plurality of scene-specific images; and
  outputting the composite image as the second video frame.

10. A system comprising:
  a communications interface;
  a non-transitory computer-readable medium; and
  one or more processors communicatively coupled to the communications interface and the non-transitory computer-readable medium, the one or more processors configured to execute processor-executable instructions stored in the non-transitory computer-readable medium to:
    obtain, from an endoscope using the communications interface and between first and second output video frames of a real-time video having a frame rate, a preliminary image of a scene during a surgical procedure, the preliminary image comprising a plurality of pixels, wherein the first and second output video frames are consecutive video frames in the real-time video;
    determine, for each pixel of the plurality of pixels, a depth within the scene;

determine first image capture parameters for the scene based on a scene illumination setting and a first set of pixels within a first range of depths in the scene;

capture, using the endoscope and between the first and second output video frames, a first image using the first image capture parameters;

determine an illumination correction for a second set of pixels at a second range of depths within the scene;

capture, using the endoscope and between the first and second output video frames, a second image using the illumination correction;

generate a composite image based on the first and second images; and output the composite image as the second output video frame.

11. The system of claim 10, wherein the one or more processors are configured to execute further processor-executable instructions stored in the non-transitory computer-readable medium to:

determine a second illumination correction for a third set of pixels at a third range of depths within the scene;

capture, between the first and second output video frames, a third image using the second illumination correction; and generate the composite image based on the third image.

12. The system of claim 10, wherein the endoscope comprises a stereoscopic endoscope, and the one or more processors are configured to execute further processor-executable instructions stored in the non-transitory computer-readable medium to:

obtain stereoscopic preliminary images;

determine, for each pixel of each stereoscopic preliminary image, the depth within the scene, capture stereoscopic first images to capture the first image;

capture stereoscopic second images to capture the second image;

generate composite stereoscopic images from the first and second stereoscopic images to generate the composite image; and output the composite stereoscopic images to output the composite image.

13. The system of claim 10, wherein the illumination correction comprises one or more of (i) adjusting a light source, (ii) adjusting an image sensor integration time, or (iii) adjusting an image sensor gain.

14. The system of claim 10, wherein the one or more processors are configured to execute further processor-executable instructions stored in the non-transitory computer-readable medium to cause a structured light project to project structured light onto the scene, and determine, for each pixel of the plurality of pixels, the depth within the scene based on detecting the structured light in the preliminary image.

15. The system of claim 10, wherein the one or more processors are configured to execute further processor-executable instructions stored in the non-transitory computer-readable medium to determine, for each pixel of the plurality of pixels, the depth within the scene using a machine learning model to estimate, for each pixel of the plurality of pixels, the depth within the scene.

16. The system of claim 10, wherein the one or more processors are configured to execute further processor-executable instructions stored in the non-transitory computer-readable medium to determine the first and second ranges of depths based on a total number of pixels in the preliminary image and a number of images to be captured between the first and second output video frames.

17. A non-transitory computer-readable medium comprising processor-executable instructions configured to cause one or more processors to:

obtain, from an endoscope and between first and second output video frames of a real-time video having a frame rate, a preliminary image of a scene during a surgical procedure, the preliminary image comprising a plurality of pixels, wherein the first and second output video frames are consecutive video frames in the real-time video;

determine, for each pixel of the plurality of pixels, a depth within the scene;

determine first image capture parameters for the scene based on a scene illumination setting and a first set of pixels within a first range of depths in the scene;

capture, using the endoscope and between the first and second output video frames, a first image using the first image capture parameters;

determine an illumination correction for a second set of pixels at a second range of depths within the scene;

capture, using the endoscope and between the first and second output video frames, a second image using the illumination correction;

generate a composite image based on the first and second images; and output the composite image as the second output video frame.

18. The non-transitory computer-readable medium of claim 17, further comprising processor-executable instructions configured to cause one or more processors to:

determine a second illumination correction for a third set of pixels at a third range of depths within the scene;

capture, between the first and second output video frames, a third image using the second illumination correction; and generate the composite image based on the third image.

19. The non-transitory computer-readable medium of claim 17, further comprising processor-executable instructions configured to cause one or more processors to:

obtain stereoscopic preliminary images;

determine, for each pixel of each stereoscopic preliminary image, the depth within the scene, capture stereoscopic first images to capture the first image;

capture stereoscopic second images to capture the second image;

generate composite stereoscopic images from the first and second stereoscopic images to generate the composite image; and output the composite stereoscopic images to output the composite image.

20. The non-transitory computer-readable medium of claim 17, wherein the illumination correction comprises one or more of (i) adjusting a light source, (ii) adjusting an image sensor integration time, or (iii) adjusting an image sensor gain.

21. The non-transitory computer-readable medium of claim 17, further comprising processor-executable instructions configured to cause one or more processors to cause a structured light project to project structured light onto the scene, and determine, for each pixel of the plurality of pixels, the depth within the scene based on detecting the structured light in the preliminary image.

22. The non-transitory computer-readable medium of claim 17, further comprising processor-executable instructions configured to cause one or more processors to determine, for each pixel of the plurality of pixels, the depth within the scene using a machine learning model to estimate, for each pixel of the plurality of pixels, the depth within the scene.

23. The non-transitory computer-readable medium of claim 17, further comprising processor-executable instructions configured to cause one or more processors to determine the first and second ranges of depths based on a total number of pixels in the preliminary image and a number of images to be captured between the first and second output video frames.

* * * * *